US009937087B2

(12) United States Patent
Weisman et al.

(10) Patent No.: US 9,937,087 B2
(45) Date of Patent: Apr. 10, 2018

(54) DISPOSABLE ABSORBENT ARTICLES COMPRISING SKIN HEALTH COMPOSITION(S) AND RELATED METHODS

(71) Applicant: The Procter & Gamble Company, Cincinnati, OH (US)

(72) Inventors: Paul Thomas Weisman, Cincinnati, OH (US); Duane Larry Charbonneau, Mason, OH (US); Serena Rae Heyse, Springboro, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 487 days.

(21) Appl. No.: 14/602,703

(22) Filed: Jan. 22, 2015

(65) Prior Publication Data

US 2015/0209202 A1    Jul. 30, 2015

Related U.S. Application Data

(60) Provisional application No. 61/931,229, filed on Jan. 24, 2014.

(51) Int. Cl.
| | | |
|---|---|---|
| *A61F 13/15* | (2006.01) | |
| *A61F 13/84* | (2006.01) | |
| *A61L 15/36* | (2006.01) | |
| *A61L 15/44* | (2006.01) | |
| *A61Q 17/00* | (2006.01) | |
| *A61Q 19/00* | (2006.01) | |
| *A61K 8/99* | (2017.01) | |
| *A61K 8/02* | (2006.01) | |

(52) U.S. Cl.
CPC ........ *A61F 13/8405* (2013.01); *A61K 8/0208* (2013.01); *A61K 8/99* (2013.01); *A61L 15/36* (2013.01); *A61L 15/44* (2013.01); *A61Q 17/005* (2013.01); *A61Q 19/00* (2013.01); *A61F 2013/8414* (2013.01); *A61L 2300/406* (2013.01)

(58) Field of Classification Search
CPC ............ A61F 2013/422; A61F 13/8405; A61F 2013/8414; A61K 8/0208; A61K 8/99; A61L 15/36; A61L 15/44; A61L 2013/8414; A61Q 17/05; A61Q 19/00
USPC ................................ 604/359, 366, 361, 367
See application file for complete search history.

(56) References Cited

U.S. PATENT DOCUMENTS 3,964,486 A   6/1976 Blaney
4,904,524 A   2/1990 Yoh
(Continued)

FOREIGN PATENT DOCUMENTS

DE   4136540   5/1992
EP   0414304   2/1991
(Continued)

OTHER PUBLICATIONS

Gilberto E. Flores, et al., "Diversity, Distribution and Sources of Bacteria in Residential Kitchens", Environmental Microbiology, pp. 1-9, 2012.
(Continued)

*Primary Examiner* — Jacqueline Stephens
(74) *Attorney, Agent, or Firm* — Richard L. Alexander

(57) ABSTRACT

The present disclosure describes disposable absorbent article(s) comprising a skin health composition effective for treating bacteria, including the bacteria associated with diaper rash.

20 Claims, 13 Drawing Sheets

(56) References Cited

U.S. PATENT DOCUMENTS

| | | | |
|---|---|---|---|
| 6,207,596 | B1 | 3/2001 | Rourke et al. |
| 6,277,399 | B1 | 8/2001 | Fischetti et al. |
| 6,479,727 | B1* | 11/2002 | Roe .................. A61F 13/42 |
| | | | 600/306 |
| 6,699,701 | B1 | 3/2004 | Sulakvelidze et al. |
| 2004/0120990 | A1* | 6/2004 | Cushman ............ A61K 9/0014 |
| | | | 424/443 |
| 2004/0167485 | A1 | 8/2004 | Gabbay |
| 2007/0154459 | A1 | 7/2007 | Hargis et al. |
| 2010/0068787 | A1 | 3/2010 | Pasternack et al. |
| 2010/0080834 | A1* | 4/2010 | Lori .................. B32B 27/32 |
| | | | 424/409 |

FOREIGN PATENT DOCUMENTS

| | | |
|---|---|---|
| WO | WO 2009060097 | 5/2009 |
| WO | WO 2009075884 | 6/2009 |

OTHER PUBLICATIONS

International Search Report and Written Opinion, PCT/US2015/012427, dated Apr. 8, 2015.

* cited by examiner

DISPOSABLE ABSORBENT ARTICLES COMPRISING SKIN HEALTH COMPOSITION(S) AND RELATED METHODS

CROSS REFERENCE TO RELATED APPLICATIONS

This application claims the benefit, under 35 USC 119(e), to U.S. Provisional Patent Application No. 61/931,229 filed on Jan. 24, 2014, which is herein incorporated by reference in its entirety.

FIELD OF THE DISCLOSURE

The present disclosure is directed to disposable absorbent articles comprising skin health composition(s), as well as methods of using the disposable absorbent articles. The articles and methods are useful for treating surfaces, including skin, that are susceptible to bacterial contamination.

BACKGROUND OF THE DISCLOSURE

Skin or other epithelial tissue can colonize pathogenic bacteria such as Streptococcus, Escherichia, Salmonella, Listeria, Shigella, Campylobacter, Clostridium, and Staphylococcus, and particularly Streptococcus, Escherichia, Salmonella, and Staphylococcus. Pathogenic bacteria can result in any of a variety of infections such as dermatitis, diaper rash, and impetigo, commonly caused by bacteria such as Escherichia coli, Staphylococcus aureus, Streptococcus pyogenes, and Staphylococcus aureus, in which elderly, infants and pre-school children are particularly susceptible. Other pathogenic conditions include other bacterial skin conditions such as urinary tract infections commonly suffered by women. Even further, moist skin surfaces, such as skin susceptible to diaper rash in infants and pre-school children are also particularly susceptible to bacterial contamination.

Unfortunately, in addition to counter-productive techniques such as using contaminated cleaning devices, other techniques have limited efficacy. Diaper rash and other infections on skin are still common problems that are difficult to manage. Improved technologies are necessary to infect, lyse, destruct, disrupt, kill, inhibit the growth of, or otherwise reduce or eliminate these bacteria on the surface of epithelial tissue. In addition to the described problems, bacteriophage are prone to have decreased activity or potency upon exposure to sunlight or ultraviolet (UV) light. Such exposure has a damaging effect on the bacteriophage, decreasing lytic ability. Absorbent articles comprising bacteriophage might also be susceptible to such decreased bacteriophage activity upon exposure to sunlight or UV light. Accordingly, there is a need for an absorbent article manufacturer to devise approaches or means for maintaining the activity of bacteriophage containing articles during distribution of the absorbent articles or components thereof from the manufacturer, to the retailer, to the consumer, and finally while being stored before use in the consumer's dwelling. The present disclosure provides disposable absorbent articles comprising skin health composition(s) useful for treating said bacteria, as well as methods of making and using the articles, as well as packages and methods of packaging the absorbent articles to preserve the composition, such as the skin health composition. The articles and methods are useful for treating surfaces, including skin, that are susceptible to bacterial contamination. These articles, and their use, provide efficacy against pathogenic bacteria in a variety of settings including in our homes, and on skin and other epithelial tissue.

SUMMARY OF THE DISCLOSURE

The present disclosure describes an embodiment comprising a disposable absorbent article comprising skin health composition(s) that may be useful for treating bacteria.

The present disclosure further describes an embodiment comprising a method of contacting a surface with one or more skin health compositions, the method comprising contacting the surface with the at least a portion of the disposable absorbent article which comprises one or more skin health compositions.

The present disclosure further describes an embodiment comprising an array of packages comprising a first package comprising a first absorbent article and a second package comprising a second absorbent article, wherein the first absorbent article comprises a bacteriophage composition and wherein the second package does not. The first package lists a first weight range and the second package lists a second weight range that overlaps with the first weight range at least in part. The first and second packages are a common brand.

The present disclosure further describes an embodiment comprising an array of packages comprising a first package comprising a first absorbent article and a second package comprising a second absorbent article, wherein the first absorbent article comprises a first skin health composition and wherein the second absorbent article comprises a second skin health composition, different from the first skin health composition. The first package lists a first weight range and the second package lists a second weight range that overlaps with the first weight range at least in part. The first and second packages are a common brand and the first and second skin health compositions are different.

The present disclosure further describes an embodiment comprising a method comprising applying a first skin health composition to a first web by a first method, applying a second skin health composition to a second web by a second method, and combining the first and second webs in the formation of an absorbent article; wherein the first and second skin health compositions are different.

The present disclosure further describes an embodiment comprising a method comprising applying a skin health composition to a web, wherein the web is used in formation of an absorbent article.

DETAILED DESCRIPTION OF THE DISCLOSURE

The disposable absorbent articles of the present disclosure comprise a composition comprising one or more bacteriophage, wherein the bacteriophage, which may be in a composition, is in releasable contact with at least a portion of the disposable absorbent article. These and other embodiments of the present disclosure are described in detail herein.

In part, these articles may be particularly advantageous because the transfer of bacteriophage to a desired surface, such as human epithelial tissue (e.g., skin or the lining of a cavity or other structure), presents a challenge in view of the non-motile nature of bacteriophage generally. This is particularly the case when the bacteriophage is incorporated into or applied to a solid material, wherein efficacy may depend in part on transfer of the bacteriophage from a solid material. Because the bacteriophage do not move after application to a solid material (aside from possible Brownian motion), they may only be effective in disrupting or otherwise harming bacterial contamination if live bacteria happens to come into contact with the fixed-position bacteriophage for a sufficient period of time. Surprisingly, it is discovered herein that the present inventive disposable absorbent articles, which comprise a bacteriophage composition, facilitate the transfer of the bacteriophage onto a surface susceptible to bacterial contamination, such as human epithelial tissue, which is sufficient to inactivate the colonized bacteria or inhibit the colonization thereof.

As used herein, a disposable absorbent article may also be referred to as an "article" or "absorbent article." In one embodiment of the present disclosure, the article is used to treat a surface that is susceptible to colonization by undesirable bacteria, such as any or a combination of bacteria described herein. In general, the surface that is susceptible to colonization by undesirable bacteria may be epithelial tissue, such as human or animal skin or a bodily cavity or other structure. In one embodiment, the surface may be human or animal skin, such as infant skin or adult skin. In another embodiment, the surface is other epithelial tissue such as urothelial tissue.

Non-limiting examples of disposable absorbent articles include diapers, training pants, adult incontinence products, and feminine hygiene products (including, for example, sanitary napkins and tampons). Other examples of a disposable absorbent articles include bandages and wound dressings.

Absorbent Article

Figure 1:
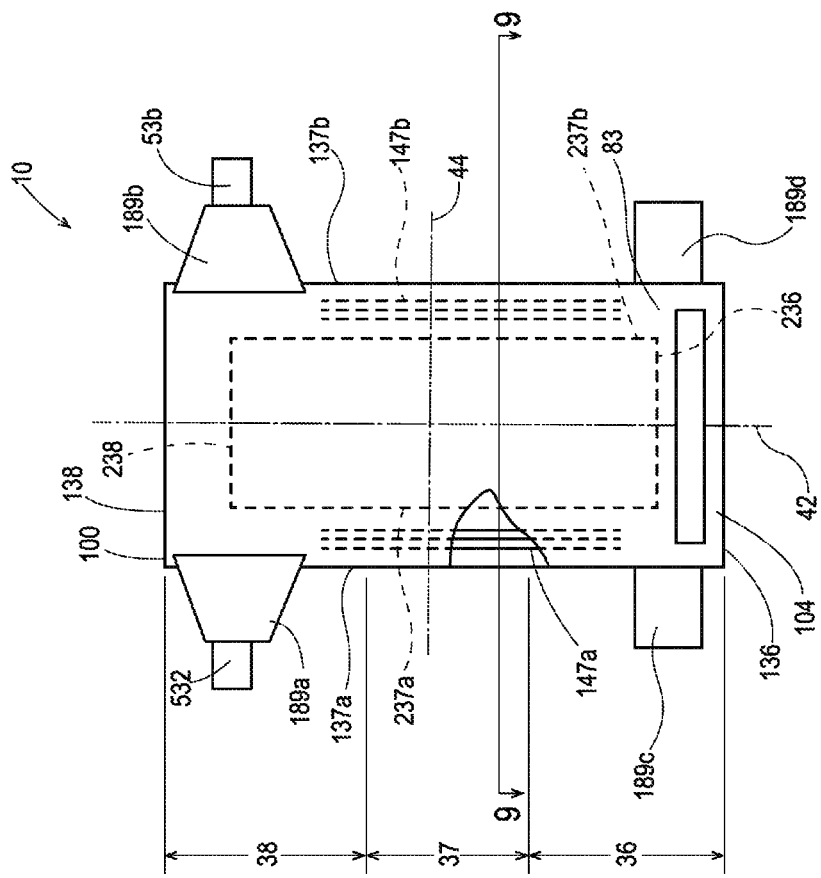
FIG. 1 is a partially cut away plan view of a taped diaper wherein the garment-facing exterior of the diaper faces the viewer.

In one embodiment, an absorbent article may comprise a chassis comprising a topsheet, a backsheet, and an absorbent core disposed at least partially between the topsheet and the backsheet. The absorbent chassis may comprise a waistband, leg cuffs and or elastic strands. In various embodiments, referring to FIG. 1, an example absorbent article 10 is shown in its flat uncontracted state prior to joining the fastening components 53a and b.

In one embodiment, referring to FIGS. 1-4 and 8, one end portion of the absorbent article 10 may be configured as a front waist region 36 and the longitudinally opposing end portion may be configured as a back waist region 38. An intermediate portion of the absorbent article 10 extending longitudinally between the front waist region 36 and the back waist region 38 may be configured as a crotch region 37. In one embodiment, although not illustrated as such, the length of each of the front waist region 36, the back waist region 38 and the crotch region 37 may be about ⅓ of the length of the absorbent article 10, for example. In other embodiments, the length of each of the front waist region 36, the back waist region 38, and the crotch region 37 may have other dimensions. In various embodiments, the absorbent article 10 may have a laterally extending front waist end edge 136 in the front waist region 36 and a longitudinally opposing and laterally extending back waist end edge 138 in the back waist region 38.

In one embodiment, referring to FIGS. 1-4 and 8, a chassis 100 of the absorbent article 10 may comprise a first longitudinally extending side edge 137a and a laterally opposing and second longitudinally extending side edge 137b. Both of the side edges 137 may extend longitudinally between the front waist end edge 136 and the back waist end edge 138. The chassis 100 may form a portion of the laterally extending front waist end edge 136 in the front waist region 36 and a portion of the longitudinally opposing and laterally extending back waist end edge 138 in the back waist region 38. Furthermore, the chassis 100 may comprise an interior surface 102, an exterior surface 104, a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 137a and through a midpoint of the second side edge 137b.

In various embodiments, a portion of or the whole absorbent article 10 may be made to be laterally extensible. The extensibility of the absorbent article 10 may be desirable in order to allow the absorbent article 10 to conform to a body of a wearer during movement by the wearer. The extensibility may also be desirable, for example, in order to allow the caregiver to extend the front waist region 36, the back waist region 38, the crotch region 37, and/or the chassis 100 to provide additional body coverage for wearers of differing size, i.e., to tailor the absorbent article 10 to the individual wearer. Such extension may provide the absorbent article 10 with a generally hourglass shape, so long as the crotch region 37 is extended to a relatively lesser degree than the waist regions 36 and/or 38. This extension may also impart a tailored appearance to the absorbent article 10 during use.

Any or all portions of the absorbent article may comprise a bacteriophage composition, wherein the bacteriophage composition, and/or levels thereof, may be the same or different for each component of the absorbent article. For example, where present, any or all of the topsheet, the absorbent core, the backsheet, the leg cuffs, the waistband, the wings, the flaps, and/or even the fastening system may comprise bacteriophage composition. Each bacteriophage composition may be the same or different, such as the same or different bacteriophage, number of bacteriophage, or levels of each bacteriophage. As used herein, when a component of the absorbent article comprises a bacteriophage composition, the bacteriophage composition may be present within that component or it may be disposed on that component as, for example, a composition printed onto the portion of the absorbent article. For simplicity, in any of these arrangements, it may be stated that the referenced component of the absorbent article comprises the bacteriophage composition.

Topsheet

In one embodiment, referring to FIGS. 2, 8, and 10-12, the absorbent article 10 may comprise a topsheet 81. The topsheet 81 may be compliant, soft feeling, and non-irritating to the wearer's skin and may be elastically stretchable in one or more directions. Further, the topsheet 81 may be liquid pervious, permitting liquids (e.g., menses, urine, and/or runny feces) to penetrate through its thickness. Various topsheets may also comprise a hydrophilic material, for example, which is configured to draw bodily fluids into an absorbent core of the chassis 100 when these fluids are expelled from the body. A suitable topsheet 81 may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 3,929,135, 4,324,246, 4,342,314, 4,463,045, 5,006,394, 5,628,097, 5,916,661, 6,545,197, and 6,107,539.

Apertured film topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet 81 comprises fibers, the fibers may be spunbond, carded, wet-laid, meltblown, hydroentangled, or otherwise processed, for example, as is generally known in the art.

The topsheet may comprise a skin care lotion. The skin care lotion may be a component of the bacteriophage composition, or it may be a separate composition. Examples of suitable lotions include, but are not limited to, those described in U.S. Pat. Nos. 5,607,760; 5,609,587; 5,635,191; 5,643,588; and 5,968,025, and as described in U.S. Application No. 61/391,353. Bacteriophage compositions may be applied onto the skin care composition, for example, in the manner described in U.S. Pat. No. 7,166,292, such that the bacteriophages sit on or be dispersed within the skin care composition to prevent the bacteriophages from saturating into the topsheet, thus migrating toward the core. Alternatively, sections of the topsheet may comprise the skin care lotion, while adjacent areas of the topsheet may comprise a bacteriophage composition. In one embodiment, the bacteriophage composition and the skin care lotion may be stripes oriented in the longitudinal direction.

In one embodiment, the topsheet may comprise graphics (e.g., 116 in FIG. 12) such that depth perception is created as described in U.S. Pat. No. 7,163,528.

Backsheet

In one embodiment, referring to FIGS. 1, 3-7, and 9-12, for example, the absorbent article 10 may comprise a backsheet 83. The backsheet 83 may be impervious, or at least partially impervious, to fluids or body exudates (e.g., menses, urine, and/or runny feces) and may be manufactured from a thin plastic film, although other flexible liquid impervious materials may also be used. The backsheet 83 may prevent the body exudates or fluids absorbed and contained in an absorbent core of the absorbent article 10 from wetting articles which contact the absorbent article 10, such as bedsheets, pajamas, clothes, and/or undergarments. The backsheet 83 may comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). A suitable backsheet may comprise a polyethylene film having a thickness of from about 0.012 mm (0.5 mils) to about 0.051 mm (2.0 mils). Examples of polyethylene films are manufactured by Clopay Corporation of Cincinnati, Ohio, under the designation BR-120 and BR-121, and by Tredegar Film Products of Terre Haute, Ind., under the designation XP-39385.

Particularly regarding feminine hygiene, one suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m$^2$ to about 35 g/m$^2$. The backsheet can be typically positioned adjacent the outer-facing surface of the absorbent core and can be joined thereto. For example, the backsheet may be secured to the absorbent core by a uniform continuous layer of adhesive, a patterned layer of adhesive, or an array of separate lines, spirals, or spots of adhesive. Illustrative, but nonlimiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods shown in U.S. Pat. Nos. 3,911,173; 4,785,996; and 4,842,666. Alternatively, the attachment device may include heat bonds, pressure bonds, ultrasonic bonds, dynamic mechanical bonds, or any other suitable attachment device or combinations of these attachment devices.

In one embodiment, the backsheet 83 may be embossed and/or matte-finished to provide a more cloth-like appearance. Further, the backsheet 83 may permit vapors to escape from the absorbent core of the absorbent article 10 (i.e., the backsheet 83 is breathable) while still preventing, or at least inhibiting, fluids or body exudates from passing through the backsheet 83. In one embodiment, the size of the backsheet 83 may be dictated by the size of the absorbent article 10 and the design or configuration of the absorbent article 10 to be formed, for example.

In one embodiment, the backsheet comprises a bacteriophage composition.

In one embodiment, an adhesive may be applied to the garment-facing exterior of the backsheet for the purpose of holding the absorbent article in place by adhering to the wearer's underwear. Such adhesive may be especially desirable for use with adult incontinence and feminine hygiene type absorbent articles.

Absorbent Core

In various embodiments, referring to FIGS. 1-4 and 8-12, the absorbent article 10 may comprise an absorbent core 200 that is disposed between the topsheet 81 and the backsheet 83. The absorbent core 200 may comprise a laterally extending front edge 236 in the front waist region 36, a longitudinally opposing and laterally extending back edge 238 in the back waist region 38, a first longitudinally extending side edge 237a, and a laterally opposing and second longitudinally extending side edge 237b. Both of the side edges 237 may extend longitudinally between the front edge 236 and the back edge 238. In one embodiment, more than one absorbent core 200 or more than one absorbent core layer may be provided in an absorbent article 10, for example. The absorbent core 200 may be any suitable size or shape that is compatible with the absorbent article 10. Example absorbent structures for use as the absorbent core 200 of the present disclosure that have achieved acceptance and commercial success are described in U.S. Pat. Nos. 4,610,678; 4,673,402; 4,888,231; and 4,834,735.

In one embodiment, suitable absorbent cores may comprise cellulosic airfelt material. For instance, such absorbent cores may comprise less than about 40%, 30%, 20%, 10%, 5%, or even 1% of the cellulosic airfelt material as determined by weight. Additionally, such an absorbent core may be primarily comprised of an absorbent gelling material in amounts of at least about 60%, 70%, 80%, 85%, 90%, 95%, or even about 100% as determined by weight. Furthermore, a portion of the absorbent core may comprise a microfiber glue (if applicable). Such absorbent cores, microfiber glues, and absorbent gelling materials are described in U.S. Pat. Nos. 5,599,335; 5,562,646; 5,669,894; 6,790,798; and 7,521,587 and in U.S. Pat. Publ. No. 2004/0158212.

In one embodiment, the absorbent core comprises a bacteriophage composition. In one such embodiment, the bacteriophage composition resides within the absorbent core. In another such embodiment, the bacteriophage composition resides on an outermost surface of the absorbent core (i.e., the bacteriophage composition may be disposed on the exterior of an outermost layer of the absorbent core). In one embodiment, the bacteriophage composition resides on the outermost surface (which may be an acquisition layer or an upper covering sheet) of the absorbent core, wherein such surface is in contact with the topsheet.

In one embodiment, the core, including multiple layers making up the core system, may be printed and embossed as described in U.S. Pat. No. 8,536,401.

Leg Cuffs

In one embodiment, referring to FIGS. 1-4, the chassis 100 of the absorbent article 10 may comprise longitudinally extending and laterally opposing leg cuffs 147a and 147b that are disposed on the interior surface of the chassis 100 that faces inwardly toward the wearer and contacts the wearer. The leg cuffs 147a and 147b may comprise one or more elastic gathering members disposed at or adjacent the proximal edge of one or both of the leg cuffs 147. In addition, to the elastic gathering members the leg cuff may also comprise one or more elastic strands disposed at or adjacent the distal edge of one or both of the leg cuffs 147. The elasticized leg cuffs 147 may comprise several embodiments for reducing the leakage of body exudates or fluids in the leg regions. The elasticized leg cuffs 147 are sometimes referred to as leg bands, barrier cuffs, elastic cuffs, or gasketing cuffs. Suitable elasticized leg cuffs 147 may comprise those described in U.S. Pat. Nos. 3,860,003, 4,909, 803, 4,695,278, 4,795,454, 4,704,115, and 4,909,803, and U.S. Pat. Publ. No. 2009/0312730. The leg cuffs 147 may be formed by folding portions of the chassis 100 laterally inward, i.e., toward the longitudinal axis 42, to form both the respective leg cuffs 147 and the side edges 137a and b of the chassis 100. In other embodiments, the leg cuffs 147 may be formed by attaching an additional layer or layers to the chassis 100 at or adjacent to each of the respective side edges 137a and 137b of the chassis 100. In one embodiment, the chassis 100 may also comprise other elastics disposed adjacent the side edges 137 which may cause the article 10 to form into a "U" shape when allowed to relax thereby pulling the interior surface 102 of the front waist region 36 toward the interior surface 102 of the back waist region 38.

In one embodiment, each leg cuff 147 may comprise a proximal edge 157a and 157b. These edges 157a and 157b are positioned proximate to the longitudinal axis 42 compared to distal edges 139a and 139b. The leg cuffs 147 may overlap the absorbent core 200, i.e., the proximal edges 157a and 157b lie laterally inward of the respective side edges 237a and 237b of the absorbent core 200. Such an overlapped configuration may be desirable in order to impart a more finished appearance to the absorbent article 10 than that imparted by a non-overlapped configuration. In other embodiments, the leg cuffs 147 may not overlap the absorbent core 200.

In one embodiment, each leg cuff 147 may be attached to the interior surface 102 of the chassis 100 in a leg cuff attachment zone (not shown) adjacent to the front waist end edge 136 and in a longitudinally opposing leg cuff attachment zone (not shown) adjacent to the back waist end edge 138. In one embodiment, between the leg cuff attachment zones, the proximal edge 157 of the leg cuff 147 remains free, i.e., not attached to the interior surface 102 of the chassis 100 or to the absorbent core 200. Also, between the longitudinally opposing leg cuff attachment zones, each leg cuff 147 may comprise one or more (specifically including one, two, three, or four elastic strands per leg cuff 147) longitudinally extensible cuff elastic gathering members 159 that may be disposed at or adjacent to the proximal edge 157 of the leg cuff 147 by any suitable methods. Each of such cuff elastic gathering members 159 may be attached over the leg cuff's entire length or over only a portion of the leg cuff's length. For example, such cuff elastic gathering members 159 may be attached only at or near the leg cuff's longitudinally opposing ends and may be unattached at the middle of the leg cuff's length. Such cuff elastic gathering members 159 may be disposed in the crotch region 37 and may extend into one or both of the front waist region 36 and the back waist region 38. For example, an elastic gathering member 159 may be attached at or adjacent to the proximal edge 157 of each of the leg cuffs 147 and extends into both the front waist region 36 and the back waist region 38.

In various embodiments, each cuff elastic gathering member 159 may be enclosed inside a folded hem for example. In various embodiments, the cuff elastic gathering members 159 may be sandwiched between two layers forming the leg cuff 147, by two layers of the chassis 100, or may be attached on a surface of the chassis 100 or the leg cuff 147 and remain exposed.

In one embodiment, when stretched, the cuff elastic gathering member 159 disposed adjacent to each leg cuff's proximal edge 157 allows the leg cuff proximal edge 157 to extend to the flat uncontracted length of the chassis 100, e.g., the length of the chassis 100. When allowed to relax, the cuff elastic gathering member 159 contracts to pull the front waist region 36 and the back waist region 38 toward each other and, thereby, bend the article 10 into a "U" shape in which the interior of the "U" shape may be formed by the portions of the article 10 that are intended to be placed toward the body of the wearer (i.e., interior surface 102). Because each of the proximal edges 157 remains free between the longitudinally oriented leg cuff attachment zones, the contractive force of the elastic gathering member 159 may lift the proximal edge 157 of the leg cuff 147 away from the interior surface 102 of the chassis 100. This lifting of the proximal edges 157 when the article 10 is in the relaxed condition lifts the leg cuffs 147 into a position to serve as side barriers to prevent, or at least inhibit, leakage of bodily exudates.

Figure 10:
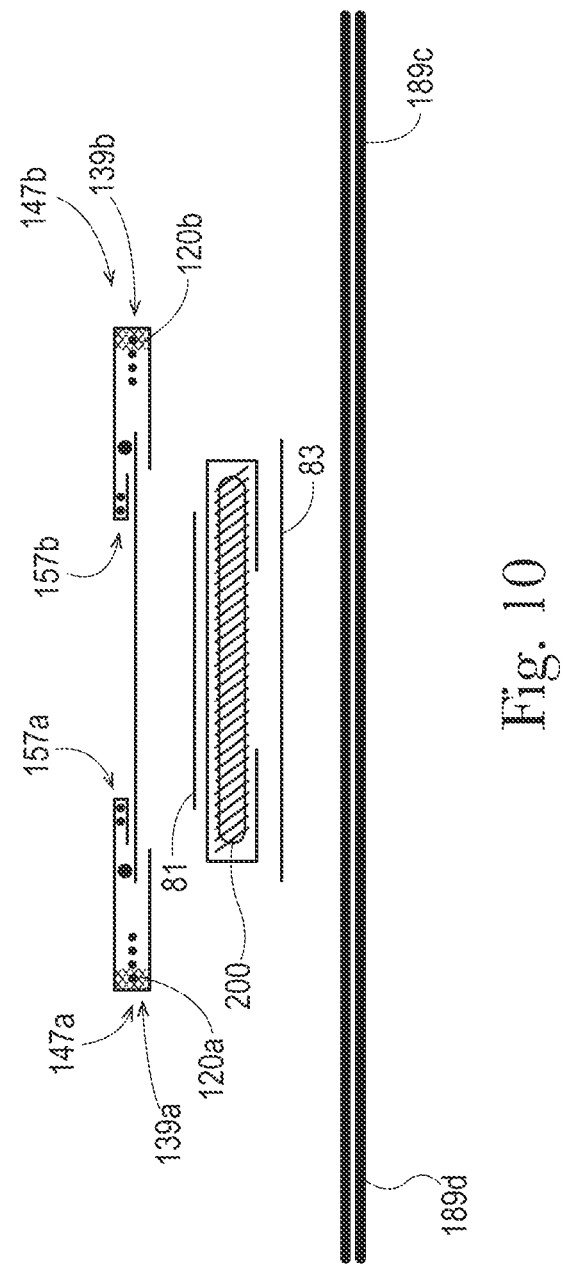
FIG. 10 is a schematic cross section view of a back belt-like flap suitable in one embodiment of the invention, taken along line 10-10 of FIG. 8.
Figure 11:
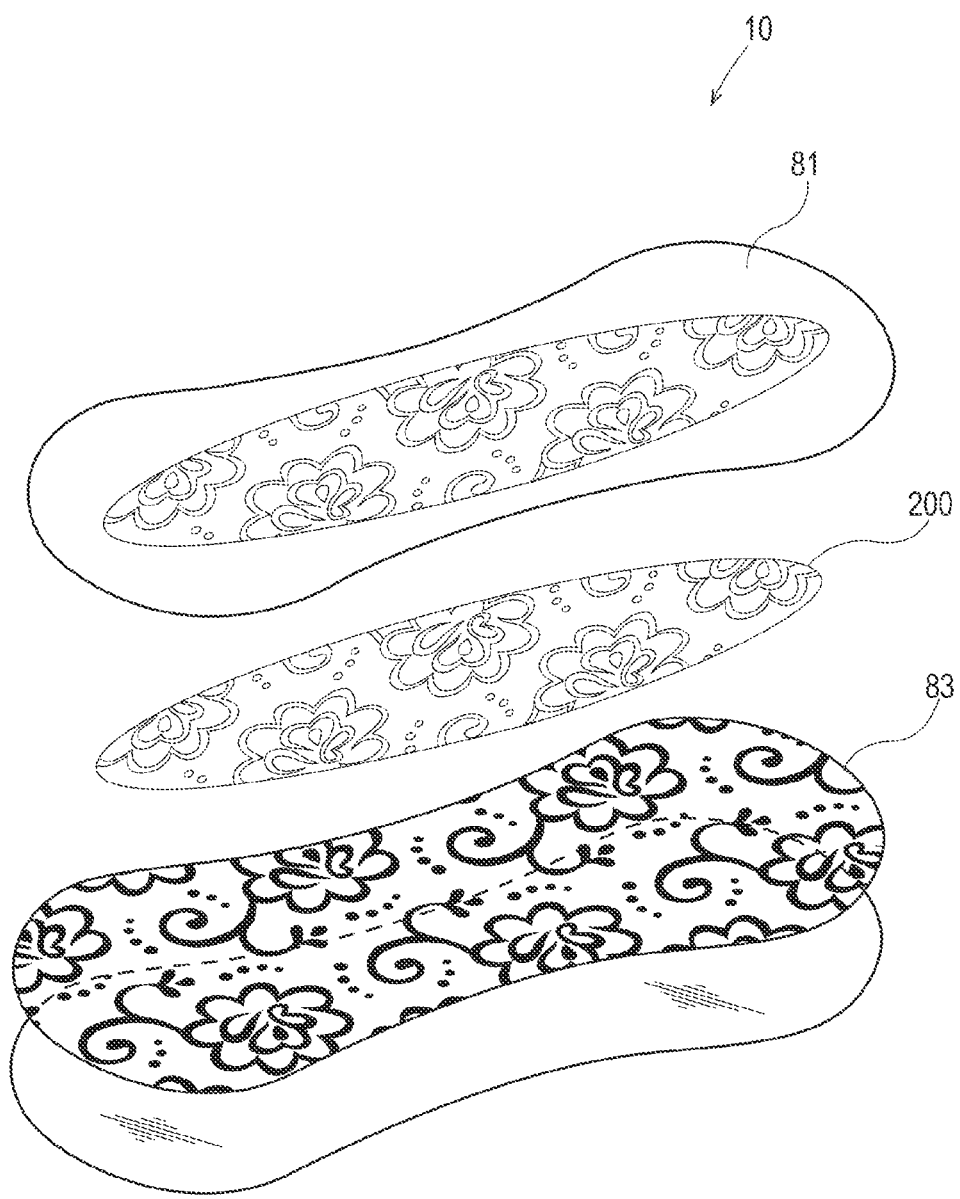
FIG. 11 is an exploded perspective view of a feminine hygiene pad.
Figure 12:
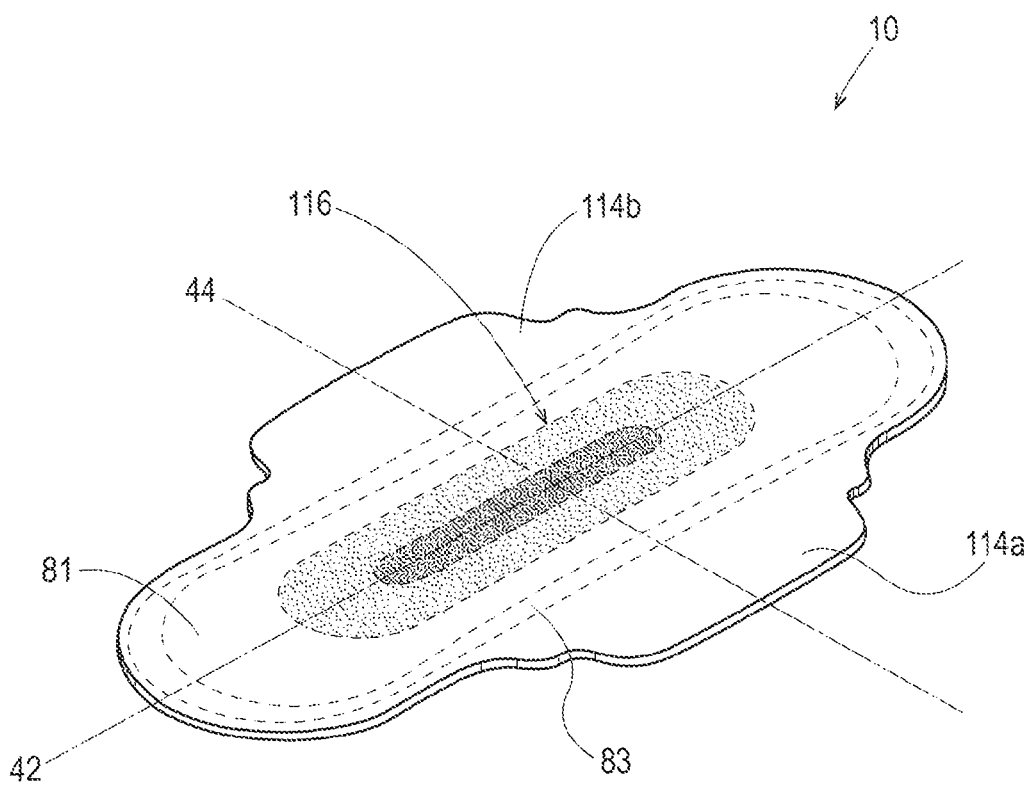
FIG. 12 is a perspective view of a feminine hygiene pad comprising wings.

In one embodiment, the bacteriophages are disposed on a wearer-facing surface, within the folded area of the cuff (see, for example, 120 FIG. 10).

Waistband

Figure 2:
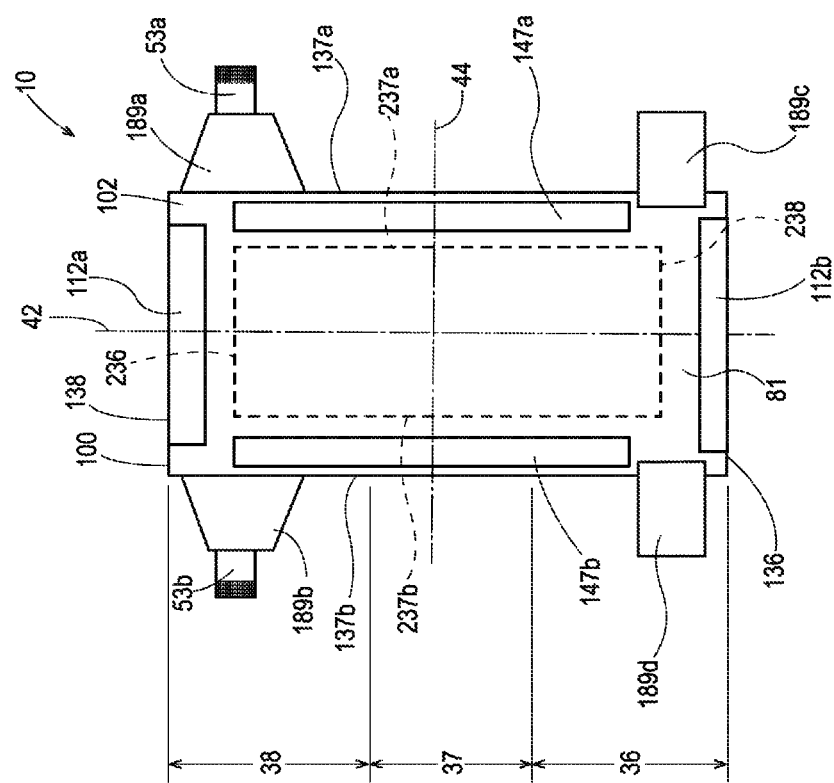
FIG. 2 is plan view of the taped diaper of FIG. 1 wherein the wearer-facing interior of the diaper faces the viewer.
Figure 3:
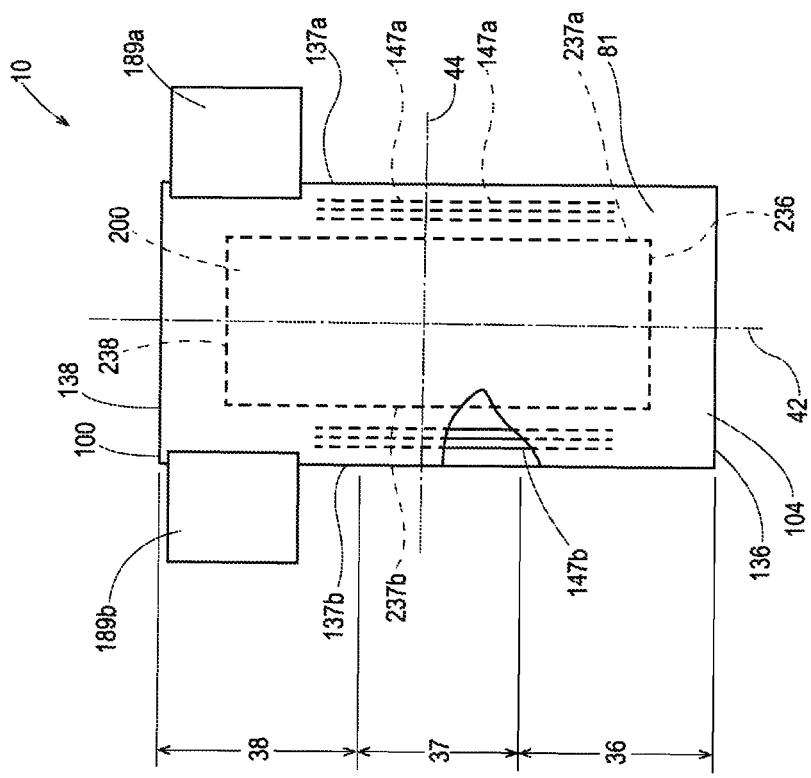
FIG. 3 is a partially cut away plan view of a pant diaper with a pair of flaps, wherein the wearer-facing interior of the diaper faces the viewer.
Figure 4:
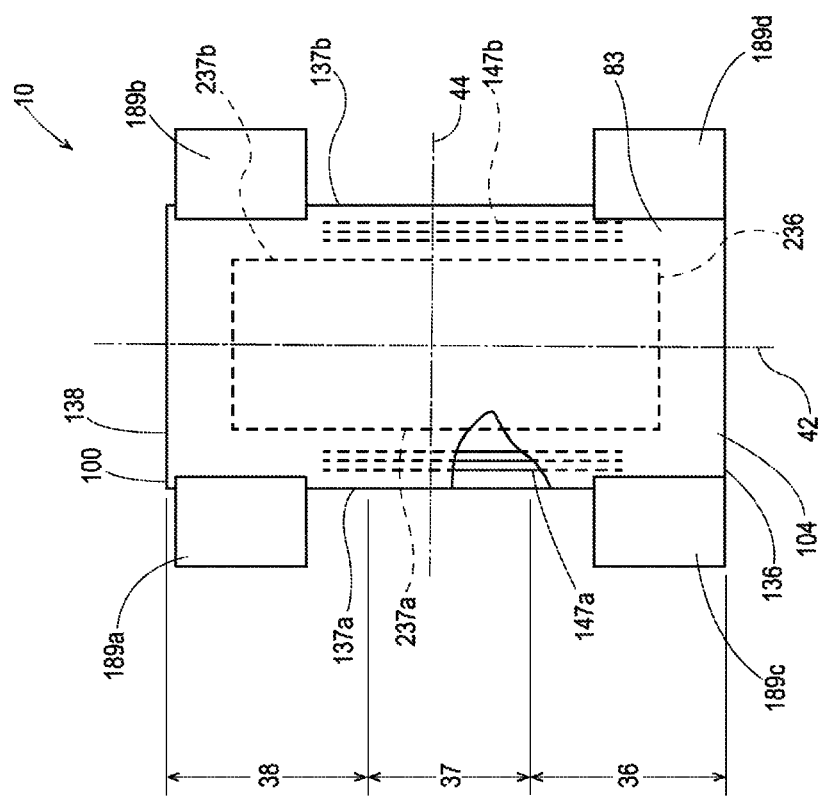
FIG. 4 is a partially cut away plan view a pant diaper with front and rear flaps, wherein the garment-facing exterior of the diaper faces the viewer.
Figure 5:
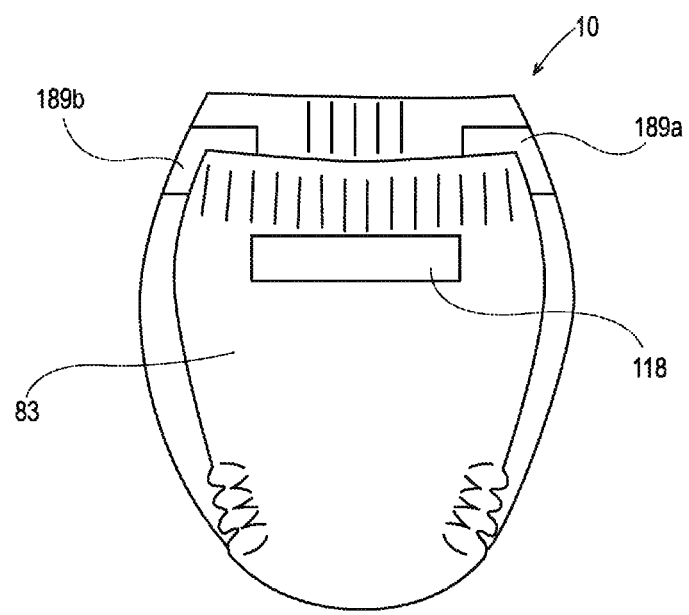
FIG. 5 is a perspective of the taped diaper shown in FIG. 1 in a folded configuration.
Figure 6:
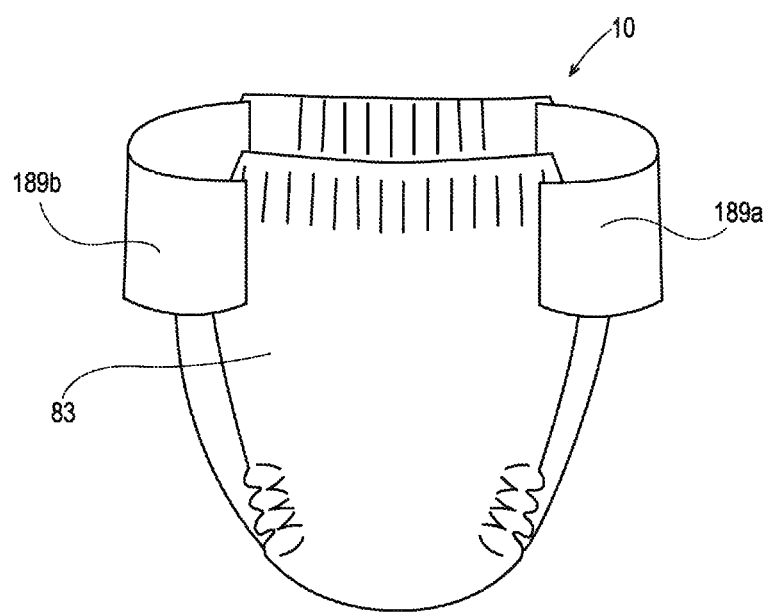
FIG. 6 is a perspective view the pant diaper shown in FIG. 3 wherein flaps connect opposing waist regions.
Figure 7:
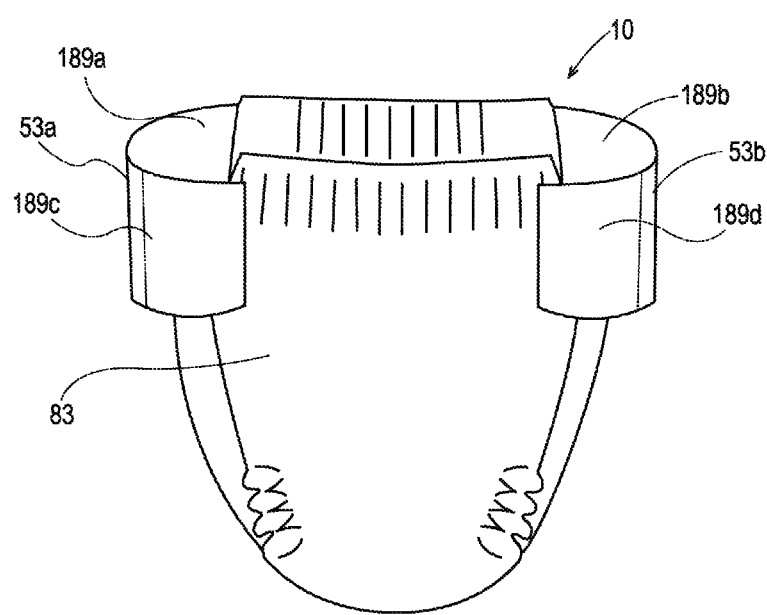
FIG. 7 is a perspective view the pant diaper shown in FIG. 4 wherein side seams connect the flaps and opposing waist regions.
Figure 8:
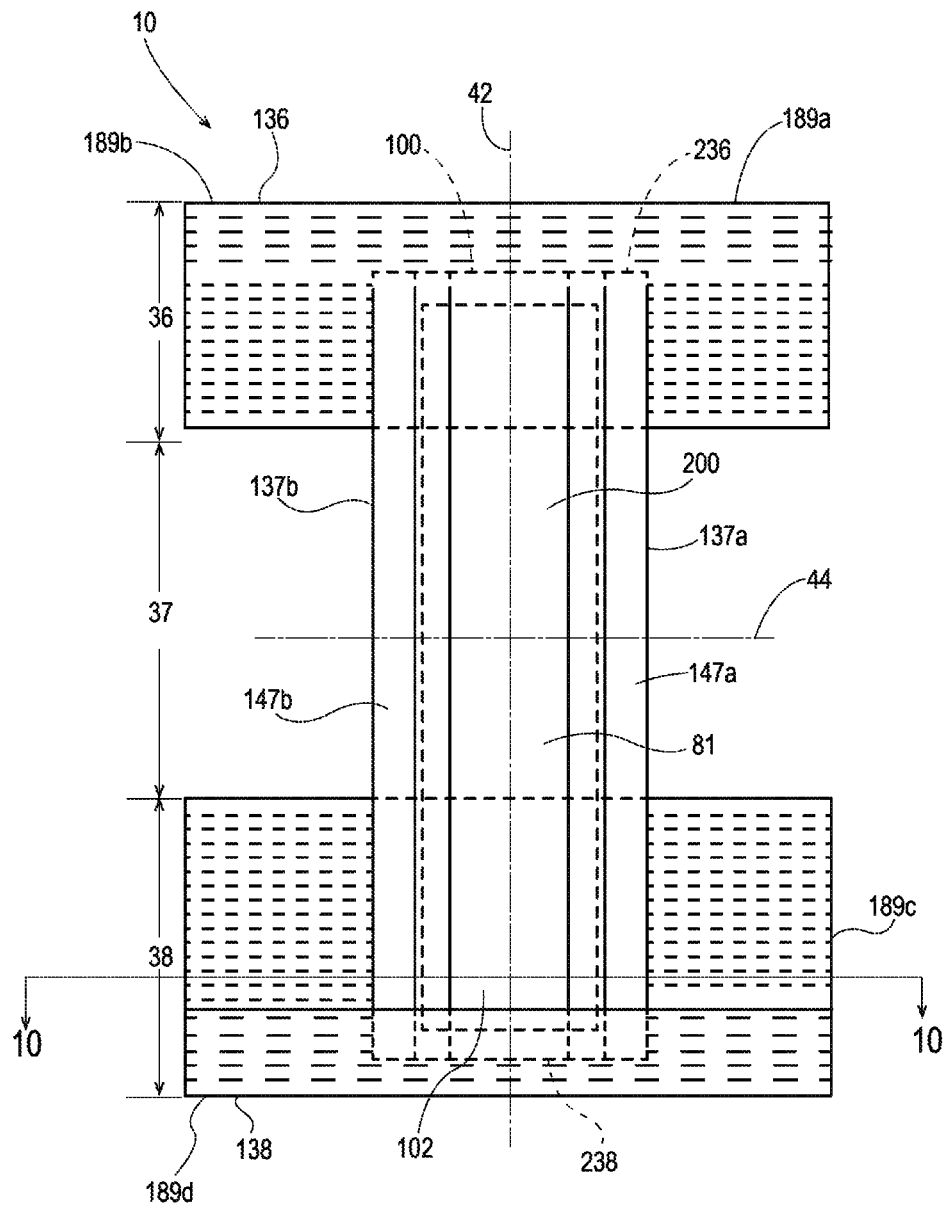
FIG. 8 is a plan view of a pant diaper with a continuous belt in the front and back waist regions.
Figure 9:
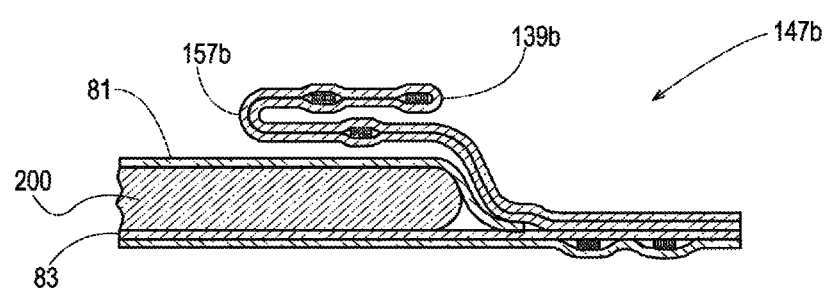
FIG. 9 is a schematic cross section view taken along line 9-9 in FIG. 1 of an example of a folded outer leg cuff suitable in one embodiment of the invention.

In one embodiment, referring to FIG. 2, the article 10 may comprise an elasticized waistband 112a and b. The elasticized waistband may provide improved fit and containment and may be configured to elastically expand and contract laterally to dynamically fit a wearer's waist. The elasticized waistband may extend longitudinally outwardly from the waist edge of the absorbent article 10 toward the waist edge of the absorbent core 200. In one embodiment, the absorbent article 10 may have two elasticized waistbands, one positioned in the back waist region 38 and one positioned in the front waist region 36, although other pant embodiments may be constructed with a single elasticized waistband. The elasticized waistband may be constructed in a number of different configurations including those described in U.S. Pat. Nos. 4,515,595 and 5,151,092.

In one embodiment, the elasticized waistbands may comprise materials that have been "prestrained" or "mechanically prestrained" (i.e., subjected to some degree of localized pattern mechanical stretching to permanently elongate the material). The materials may be prestrained using suitable deep embossing techniques. In other embodiments, the materials may be prestrained by directing the material through an incremental mechanical stretching system as described in U.S. Pat. No. 5,330,458. The materials may then be allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

Flaps

The flaps 189(a-d) may be discrete from or integral with the chassis 100. A discrete flap is formed as separate element which is joined to the chassis 100. In some embodiments, this includes a plurality of flaps, e.g. 2 or 4 (often referred to as ear panels or side flaps) being joined to the side edges 137a and b of the chassis in the front and/or rear waist regions 36 and 38 (see FIGS. 1-7). In other embodiments this may include a front and/or back belt-like flaps being joined across the front and back (or rear) waist regions of the chassis 100, at least across end edges of the chassis 136 and 138 (see FIGS. 8 and 10). In some embodiments the waistbands 112 can overlap the flaps to create a continuous belt-like structure (not shown).

The belt-like flaps and may comprise an inner nonwoven layer and an outer nonwoven layer and elastics therebetween. The inner and outer nonwoven layers may be joined using adhesive or thermoplastic bonds. Various suitable belt-like flap configurations can be found in U.S. Pub. No. 2013-0211363.

An integral flap is a portion, one or more layers, of the chassis that projects laterally outward from the longitudinal edge. The integral flap may be formed by cutting the chassis to include the shape of the flap projection.

While many of the embodiments illustrated in this application having belt-like flaps are pant articles, taped articles may have belt-like flaps disposed in one or both waist regions as well.

Fastening System

The absorbent article may also include a fastening system. When fastened, the fastening system interconnects the front waist region 36 and the rear waist region 38 resulting in a waist circumference that may encircle the wearer during wear of the absorbent article 10. This may be accomplished by flaps 189a and b in the back waist region interconnecting with flaps 189c and d in the front waist region or by flaps in the back waist region interconnecting with the chassis 100 in the front waist region. The fastening system may comprises a fastener 53a and b such as tape tabs, hook and loop fastening components, interlocking fasteners such as tabs & slots, buckles, buttons, snaps, and/or hermaphroditic fastening components, although any other known fastening means are generally acceptable. The fasteners may releasably engage with a landing zone 118, which may be a woven or nonwoven. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system may also provide a means for holding the article in a disposal configuration as disclosed in U.S. Pat. No. 4,963,140. The fastening system may also include primary and secondary fastening systems, as disclosed in U.S. Pat. No. 4,699,622. The fastening system may be constructed to reduce shifting of overlapped portions or to improve fit as disclosed in U.S. Pat. Nos. 5,242,436; 5,499,978; 5,507,736; and 5,591,152.

Wings

The absorbent article may comprise "wings" (114a and b in FIG. 12) intended to wrap the edges of the wearer's undergarments in the crotch region and/or affix the article to the undergarment to avoid poor folding and premature detachment. Exemplary absorbent articles comprising wings are disclosed in U.S. Pat. No. 8,039,685.

The Bacteriophage Composition

The articles of the present disclosure comprise a composition comprising one or more bacteriophage and may be referred to as a "bacteriophage composition." When the bacteriophage composition comprises bacteriophage effective against treating the bacteria associated with an infection of the skin, such as diaper rash, the bacteriophage composition may be referred to as a "skin health composition." In one embodiment herein, the bacteriophage composition comprises two or more bacteriophage. In another embodiment herein, the bacteriophage composition comprises three or more bacteriophage. In another embodiment herein, the bacteriophage composition comprises four or more bacteriophage. For example, in one embodiment, the bacteriophage composition comprises six bacteriophage, such as LISTSHIELD™ (LMP-102™), commercially available from Intralytix, Inc., Baltimore, Md.

As used herein, the term "bacteriophage" refers to a particular bacteriophage that is effective against one or more bacterial strains. As used in this context, "effective against" means that the referenced bacteriophage infects, lyses, destructs, disrupts, kills, inhibits the growth of, reduces, inactivates or is otherwise effective against to the referenced strain of bacteria. In one embodiment, the bacteriophage is a lytic bacteriophage, and therefore is capable of infecting and killing the target bacteria. As used herein, "bacteria" or "target bacteria" refer to an undesirable microorganism susceptible to infection, lysis, destruction (e.g., apoptosis), disruption, death, or inhibited growth, or any alternate mode of cell death caused by a bacteriophage. Different bacteriophage may infect different strains of bacteria with different results, or may infect some strains of bacteria but not others. In one embodiment, the bacteria or target bacteria is pathogenic bacteria (i.e., bacteria that are capable of causing infection). However, other bacteria, such as bacteria that are the source of malodor or other undesirable characteristics, are appropriate target bacterial as well.

The bacteriophage may be, independently, wild-type or genetically modified, or any combination thereof. In one embodiment, one or more of the bacteriophage present in the bacteriophage composition are wild-type. In another embodiment, all of the bacteriophage present in the bacteriophage composition are wild-type.

In one embodiment of the present disclosure, one or more of the bacteriophage is a lytic bacteriophage, and is therefore capable of infection, destruction, and bacterial cell death.

In one embodiment of the present disclosure, one or more of the bacteriophage is of the taxonomic family selected from the group consisting of Siphoviridae, Podoviridae, Myoviridae, and any combinations thereof. In one embodiment, one or more of the bacteriophage is of the taxonomic family Myoviridae. In one embodiment, all of the bacteriophage is of the taxonomic family Myoviridae.

In one embodiment herein, one or more of the bacteriophage is a lytic bacteriophage of the taxonomic family Myoviridae. In a further embodiment, wherein the bacteriophage composition comprises two or more bacteriophage, then two or more of the bacteriophage are a lytic bacteriophage of the taxonomic family Myoviridae. In a further embodiment, wherein the bacteriophage composition comprises three or more bacteriophage, then three or more of the bacteriophage are a lytic bacteriophage of the taxonomic family Myoviridae.

In one embodiment herein, the bacteriophage is a lytic bacteriophage of the taxonomic family Myoviridae and the taxonomic subfamily Teequatrovirinae. In one embodiment, the bacteriophage is a lytic T4 phage. Non-limiting examples include Enterobacteria phage T2, Enterobacteria phage T4, Enterobacteria phage T6, phage JS10, phage JS98, phage R851, and any combinations thereof.

In one embodiment herein, the bacteriophage is effective against gram-positive pathogenic bacteria. In one embodiment herein, the bacteriophage is effective against gram-negative pathogenic bacteria. In one embodiment, herein the bacteriophage cocktail is effective against a combination of gram-negative and gram-positive pathogenic bacteria.

In one embodiment herein, the bacteriophage is effective against Enterobacterium such as, for example, *Salmonella, Escherichia*, or *Shigella*. Additionally or alternatively, one of more of the bacteriophage is effective against a strain of bacteria of a taxonomic genus selected from the group consisting of *Streptococcus, Escherichia, Salmonella, Listeria, Shigella, Campylobacter, Clostridium, Staphylococcus, Pseudomonas, Mycobacterium*, and any combinations thereof. In one embodiment, one of more of the bacteriophage is effective against a strain of bacteria of a taxonomic genus selected from the group consisting of *Streptococcus, Escherichia, Salmonella, Listeria, Staphylococcus, Pseudomonas*, and any combinations thereof.

In one embodiment herein, the bacteriophage is effective against *Streptococcus*. In one embodiment, the *Streptococcus* bacteria is *Streptococcus pyogenes*.

In one embodiment herein, the bacteriophage is effective against *Escherichia*. In one embodiment, the *Escherichia* bacteria is *Escherichia coli*.

In one embodiment herein, the bacteriophage is effective against *Salmonella*. In one embodiment, the *Salmonella* bacteria is selected from the group consisting of *Salmonella enteritidis, Salmonella typhimurium, Salmonella heidelberg, Salmonella newport, Salmonella hadar*, and any combinations thereof. In one embodiment, the *Salmonella* bacteria is *Salmonella enteritidis*. In one embodiment herein, the bacteriophage is a combination of bacteriophage such as, for example, SALMOLYSE™, containing six bacteriophage and commercially available from Intralytics, Inc., Baltimore, Md. In one embodiment herein, the bacteriophage is a combination of bacteriophage such as, for example, SALMOFRESH™, containing six bacteriophage and commercially available from Intralytix, Inc., Baltimore, Md. In one embodiment herein, the bacteriophage may be, for example, SALMONELEX™, a broad-spectrum combination of bacteriophage commercially available from Micreos B.V.

In one embodiment herein, the bacteriophage is effective against *Listeria*. In one embodiment, the *Listeria* bacteria is *Listeria monocytogenes*. In one embodiment herein, the bacteriophage is a combination of bacteriophage such as, for example, LISTSHIELD™ (LMP-102™), containing six bacteriophage and commercially available from Intralytix, Inc., Baltimore, Md. In one embodiment herein, the bacteriophage may be, for example, LISTEX™ P100, a broad-spectrum combination of bacteriophage commercially available from Micreos B.V.

In one embodiment herein, the bacteriophage is effective against *Shigella*. In one embodiment, the *Shigella* bacteria is *Shigella sonnei* or *Shigella flexneri*.

In one embodiment herein, the bacteriophage is effective against *Campylobacter*. In one embodiment, the *Campylobacter* bacterium is *Campylobacter jejuni*.

In one embodiment herein, the bacteriophage is effective against *Clostridium*. In one embodiment, the *Clostridium* bacterium is *Clostridium botulinum*.

In one embodiment herein, the bacteriophage is effective against *Staphylococcus*. In one embodiment, the *Staphylococcus* bacteria is *Staphylococcus aureus*.

In one embodiment herein, the bacteriophage is effective against *Pseudomonas*. In one embodiment, the *Pseudomonas* bacteria is *Pseudomonas aeruginosa*.

In one embodiment herein, the bacteriophage is effective against *Mycobacterium*. In one embodiment, the *Mycobacterium* bacteria is *Mycobacterium tuberculosis*.

In one embodiment, at least two absorbent article components comprise the same or different bacteriophage. For example, the topsheet may comprise bacteriophage composition A (which may comprise one or a composition of bacteriophage) and the absorbent core may comprise bacteriophage composition A as well. As another example, the topsheet may comprise bacteriophage A (which may comprise one or a composition of bacteriophage) and the cuffs comprise bacteriophage composition B (which may comprise one or a composition of bacteriophage, but is compositionally different relative to bacteriophage composition A).

In one embodiment, at least three absorbent article components comprise the same or different bacteriophage. For example, the topsheet may comprise bacteriophage composition A (which may comprise one or a composition of bacteriophage) and the cuffs and an acquisition layer of the core may comprise bacteriophage composition A as well. In another embodiment, the cuffs and/or acquisition layer of the core may comprise bacteriophage composition B (which may comprise one or a composition of bacteriophage, but is compositionally different relative to bacteriophage composition A).

In one embodiment, from two to four different absorbent article components may each comprise a unique bacteriophage composition, relative to any other component of the absorbent article.

Two, three, and/or four or more absorbent article components may comprise the same or different bacteriophage composition in different concentrations. One of ordinary skill of the art, with the benefit of this disclosure, will readily determine the level of bacteriophage composition suitable for inclusion with respect to any given component of the absorbent article herein.

The articles of the present disclosure may comprise at least about $1\times10^1$ PFUs (as is commonly understood in the art, plaque forming units) or at least about $1\times10^2$ PFUs of the one or more bacteriophage or at least $1\times10^3$ PFUs of the one or more bacteriophage or at least $1\times10^4$ PFUs of the one or more bacteriophage or at least $1\times10^5$ PFUs of the one or more bacteriophage or at least $1\times10^6$ PFUs of the one or more bacteriophage. In another embodiment herein, the articles comprise from about $1\times10^1$ PFUs to about $1\times10^{12}$ PFUs of the one or more bacteriophage. In yet another embodiment herein, the articles comprise from about $1\times10^3$ PFUs to about $1\times10^8$ PFUs of the one or more bacteriophage. In yet another embodiment herein, the articles comprise from about $1\times10^3$ PFUs to about $1\times10^6$ PFUs of the one or more bacteriophage.

One or a combination of the absorbent article components (including the topsheet, backsheet, leg cuffs, absorbent core, flaps and waistband) of the present disclosure may comprise at least about $1\times10^1$ PFUs or at least about $1\times10^2$ PFUs of the one or more bacteriophage or at least $1\times10^3$ PFUs of the one or more bacteriophage or at least $1\times10^4$ PFUs of the one or more bacteriophage or at least $1\times10^5$ PFUs of the one or more bacteriophage or at least $1\times10^6$ PFUs of the one or more bacteriophage. In another embodiment herein, one or a combination of the absorbent article components comprise from about $1\times10^1$ PFUs to about $1\times10^{12}$ PFUs of the one or more bacteriophage. In yet another embodiment herein, one or a combination of the absorbent article components comprise from about $1\times10^3$ PFUs to about $1\times10^8$ PFUs of the one or more bacteriophage. In yet another embodiment herein, the articles comprise from about $1\times10^3$ PFUs to about $1\times10^6$ PFUs of the one or more bacteriophage. The bacteriophages may be disposed on a wearer and/or garment-facing surface of one or more of the absorbent article components.

An absorbent article may comprise least about $1\times10^1$ PFUs or at least about $1\times10^2$ PFUs of the one or more bacteriophage or at least $1\times10^3$ PFUs of the one or more bacteriophage or at least $1\times10^4$ PFUs of the one or more bacteriophage or at least $1\times10^5$ PFUs of the one or more bacteriophage or at least $1\times10^6$ PFUs of the one or more bacteriophage per square centimeter of a component of the disposable absorbent article. In another embodiment herein, the absorbent article may comprise from about $1\times10^1$ PFUs to about $1\times10^9$ PFUs of the one or more bacteriophage per square centimeter of the a component of the disposable absorbent article. In yet another embodiment herein, the absorbent article may comprise from about $1\times10^3$ PFUs to about $1\times10^6$ PFUs of the one or more bacteriophage per square centimeter of a component of the disposable absorbent article.

Indicia

In one embodiment, it may be useful for the disposable adsorbent article to comprise indicia for communication to a user that a bacteriophage composition is present. For example, employing a top sheet within a diaper or adult incontinence product, it is possible that the bacteriophage composition resides on the wearer-facing surface of a top sheet. In order to ensure that it is evident that at least a portion of the bacteriophage composition contacts the surface that is susceptible to bacterial contamination, the disposable adsorbent article may comprise a component, such as a topsheet, a backsheet, or an absorbent core, which could contain an indicator such as a sensor, colors, ink, dye, pigment, shading, design, picture, word, symbol, graphic, image, diaper wetness indicator or any combination thereof, or any of a variety of other indicators that communicates to the wearer or caretaker that the article comprises the bacteriophage composition.

In addition, other indicia could indicate that at least a portion of the bacteriophage composition has been transferred from the article to the surface susceptible to bacterial contamination while in use. Continuing with the non-limiting example of the diaper, the backsheet could contain a colored indicator that communicates that a certain amount of bacteriophage composition resides on the topsheet (for example) of the diaper, and this colored indicator could change in some manner once at least a portion of the bacteriophage composition is transferred from the article to the desired surface (e.g., a baby's skin). The article may contain an indicator such as a sensor, colors, ink, dye, pigment, shading, design, picture, word, symbol, graphic, image, diaper wetness indicator or any combination thereof, or any of a variety of other indicators that communicates to the user that transfer has occurred.

The indicia may be present on the articles via any of a variety of different mechanisms such as, for example, printing, coating, or embossing, the indicia onto a surface of a component of the article. In some embodiments, an indicia will also be present on the packaging material containing the articles of the invention. The package indicia may have a functional relationship with the articles in the package to better inform the wearer or caretaker of the particular location of the bacteriophage on/in the article. For example, the article and the package indicia may comprise the same symbol, wherein the package indicia makes it clear that said symbol on the article represents the location of the bacteriophage(s).

Methods of Applying Bacteriophages of the Present Disclosure to a Wearer

The present disclosure is further directed to methods of contacting a surface with one or more bacteriophage, comprising contacting the surface with an article herein. The surface may be any surface that is susceptible to bacterial contamination. To illustrate, the surface may be epithelial tissue of a human or other animal (including, for example, a companion animal such as a dog or cat). In one embodiment, the surface susceptible to bacterial contamination is human skin or the epithelial surface of a cavity or other body structure. For example, the epithelial surface may be urothelial tissue (susceptible to, for example, bacterial urinary tract infection) or infant or toddler skin that is often in contact with absorbent articles such as diapers or training pants.

In one embodiment herein, at least a portion of the one or more bacteriophage is releasably transferred from the article to the surface. In one embodiment, from about $1\times10^1$ PFUs to about $1\times10^{10}$ PFUs of the one or more bacteriophage is releasably transferred from the article to the surface.

In one embodiment, such transfer is readily accomplished wherein the bacteriophage composition is contained on a surface of the article that may come in contact with the surface that is susceptible to bacterial contamination. For example, with respect to a disposable diaper, the article may comprise bacteriophage composition on the wearer-facing surface of the topsheet (the surface of the diaper that comes into contact with skin and other epithelial tissue) of the diaper.

In one embodiment, the bacteriophage composition release is delayed. For instance, the bacteriophages are released after the wearer moves around for a period of time, or after the wearer insults the absorbent article. Delay of release of the bacteriophages may be accomplished by formulations that release the bacteriophages when wetted. Other mechanisms include placement of the bacteriophage composition two or more layers away from the wearer, such that a urine insult puts the bacteriophages in fluid communication with the wearer. Another mechanism includes encapsulation of the bacteriophages, such that the capsules break due to movement stresses, a solvent, etc.

Methods of Applying Bacteriophages of the Present Disclosure to an Absorbent Article In one embodiment, bacteriophage compositions of the present disclosure may be applied to one or more components of the absorbent articles via printing (e.g., via ink jet) and/or by coating (e.g., slot coating). Bacteriophage compositions may be applied to continuous precursor webs as the webs travel in the machine direction. For instance, the topsheet precursor web may receive the bacteriophage composition prior to being joined to one or more other webs (e.g., the backsheet web), and prior to the final knife that creates discrete absorbent articles. Alternatively, bacteriophage compositions may be applied to each of the discrete absorbent article.

In one embodiment of making absorbent articles of the present disclosure, one bacteriophage may be applied via application method A (e.g., slot coating) while the same or different bacteriophage is applied via method B (e.g., ink jet printing), which is different from method A.

Array of Absorbent Articles Comprising a Bacteriophage

In one embodiment, different sizes of absorbent articles comprise different bacteriophage.

In one embodiment, absorbent articles having different absorbent article components, like those disclosed in U.S. Pat. No. 6,648,864, may comprise different bacteriophage. In another embodiment, absorbent article designed for wearers having different stages of development, as disclosed in U.S. Pat. No. 6,648,864, have different bacteriophage.

EXAMPLES

This example demonstrates the transfer of bacteriophage from an article of the present disclosure onto a surface such as skin.

Method:
1. Prepare pig skin
   a. cut 7, ~2"×1" squares of pig skin with ethanol sterilized scissors
   b. Place cut skin squares into a large petri plate (1 square/plate)
2. Cut 6, 6"×6" squares of diaper top sheet
3. Prepare a working surface by laying down three pieces of foil (larger than 6"×6")
4. Add 1 diaper top sheet onto a foil surface
   a. Spray 10 times with T4 lysate
   b. Repeat for 2 more top sheets
   c. Allow to dry
5. Fold top sheet in half 3 times
6. Wipe top sheet across a square of pig skin 10 times using sterile forceps
   a. Repeat with fresh pig skin piece for remaining phage treated top sheets
   b. Repeat with fresh pig skin piece for remaining non-phage treated top sheets (neg controls)
7. Place pig skin samples in 20 ml sterile saline in a 50 ml conical
   a. Vortex 30 s
   b. Pass saline through a 0.2 um filter and collect filtrate
8. Complete positive control
   a. Add 75 ul of phage directly onto a pig skin sample
   b. Place pig skin sample into 20 ml sterile saline in a 50 ml conical
   c. Vortex for 30 s
   d. Pass saline through a 0.2 um filter and collect filtrate
9. Complete plaque assay on collected filtrates (using *E. coli* 13303)
   a. Dilute phage test samples to $10^{-5}$ insaline
      i. Add 1 ml of dilutions undiluted to $10^{-5}$ to 1.5 ml sterile microcentrifuge tubes
   b. Dilute positive control to $10^{-7}$ insaline
      i. Add 1 ml of dilutions $10^{-5}$ to $10^{-7}$ to 1.5 ml sterile microcentrifuge tubes
   c. Add 1 ml of each undiluted negative control to a 1.5 ml sterile microcentrifuge tube
   d. Add 100 ul of the overnight 13303 culture to each tube
      i. Allow to incubate at RT for 10 minutes
   e. Add each bacteria/phage solution to a 5 ml tube of top agar
      i. Mix gently
   f. Pour onto a TSA plate
      i. Allow to harden
      ii. Invert and incubate at 36° C. overnight
10. At least 16 hours later, count the number of plaques observed on each plate and record Results:

|  | Dilution | Plate Count | pfu/mL | LOG |
|---|---|---|---|---|
| Positive control | | | | |
| Replicate 1 | 5 | 70 | 7.00E+06 | 6.8451 |
| Replicate 1 | 6 | 11 | 1.10E+07 | 7.0414 |
| Replicate 1 | 7 | 2 | 2.00E+07 | 7.3010 |
| Pig Skin (neg controls) | | | | |
| Replicate 1 | 0 | 150 | 1.50E+02 | 2.1761 |
| Replicate 2 | 0 | 149 | 1.49E+02 | 2.1732 |
| Replicate 3 | 0 | 63 | 6.30E+01 | 1.7993 |
| | | AVERAGE | 1.21E+02 | 2.0816 |
| Pig Skin Transfer | | | | |
| Replicate 1 | 4 | 45 | 4.50E+05 | 5.6532 |
| Replicate 2 | 4 | 98 | 9.80E+05 | 5.9912 |
| Replicate 3 | 5 | 25 | 2.50E+06 | 6.3979 |
| | | AVERAGE | 1.31E+06 | 6.1173 |
| Avg total recovered/skin sample | | | 2.62E+07 PFU | |
| | | | 7.42 log PFU | |

Packages

Absorbent articles comprising the bacteriophage composition of the present disclosure may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package.

Accordingly, packages of the absorbent articles comprising the bacteriophage composition according to the present disclosure may have an in-bag stack height of less than about 80 mm, less than about 78 mm, or less than about 76 mm, according to the In-Bag Stack Height Test described herein. Alternatively, packages of the absorbent articles of the present disclosure may have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test described herein. These stack heights may be desirable for protecting against ultraviolet light, which may be responsible for degrading the effectiveness of the bacteriophage compositions of the present disclosure. Particularly, as the bacteriophage containing surfaces of the absorbent article are compressed, ultraviolet light is not able to penetrate the inner portions of the absorbent articles, thus preserving the integrity and activity of the bacteriophage composition. Further details regarding in-back stack height are disclosed in U.S. Pat. No. 8,585,666, to Weisman et al., issued on Nov. 19, 2013.

In combination with stack height, or as an alternative to it, the absorbent articles may be folded, including bifolded or trifolded. This will also act to keep ultraviolet light from coming into contact with the bacteriophage(s).

Further, in combination with stack height and folding, the absorbent articles may be placed in packages that are opaque or nearly opaque, such that no light, or very little light is able to penetrate the package.

In-Bag Stack Height Test

The in-bag stack height of a package of the absorbent articles of the present disclosure is determined as follows:

Equipment

Universal Diaper Packaging Tester (UDPT) (Model #M-ROEL; Machine #MK-1071), including a horizontal sliding plate (horizontal plate that moves up and down in a vertical plane) for adding weights. It is counter-balanced by a suspended weight to assure that no downward force is added from the horizontal sliding plate assembly to the diaper package at all times. The UDPT is available from Matsushita Industry Co. LTD, 7-21-101, Midorigaoka-cho, Ashiya-city, Hyogo JAPAN. Zip code: 659-0014. A 850 g (+/−0.5 g) weight.

Definitions

Figure 13:
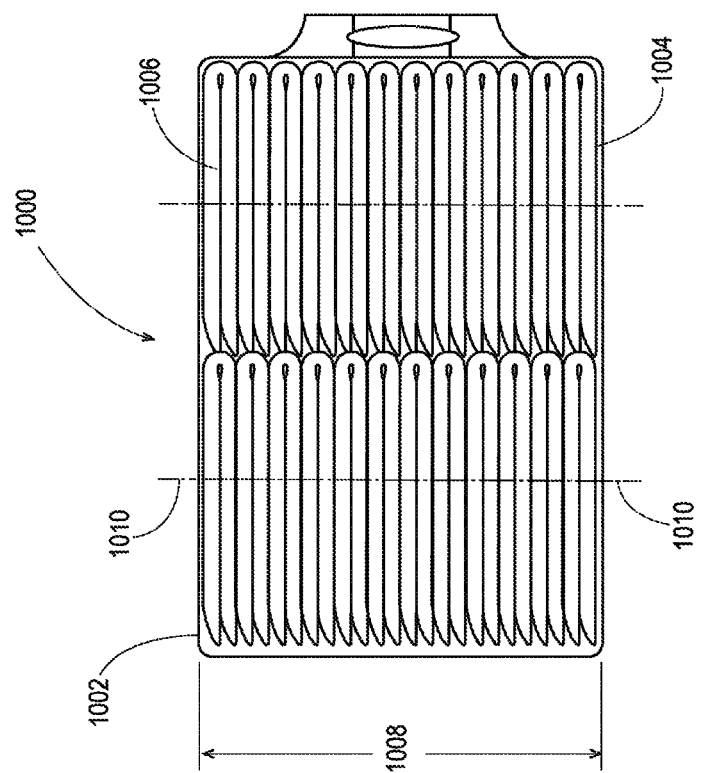
FIG. 13 is a side view of a package of absorbent articles showing the package width. The outer surface is illustrated as transparent for purposes of clarity.

As illustrated in FIG. 13, a package 1000 defines an interior space 1002 and comprises a plurality of absorbent articles 1004. The absorbent articles are in a stack 1006. The package has a package width 1008. The package width 1008 is defined as the maximum distance between the two highest bulging points along the same compression stack axis 1100 of the absorbent article package 1000.

In-Bag Stack Height=(Package Width/Pad Count Per Stack)×10 absorbent articles.

Apparatus Calibration

Pull down the horizontal sliding plate until its bottom touches the tester base plate. Set the digital meter located at the side of the horizontal sliding scale to zero mark.

Raise the horizontal sliding plate away from the tester base plate.

Test Procedure

Put one of the side panel of the absorbent article package along its width standing at the center of the tester base plate.

Make sure the vertical sliding plate (vertical plate that moves left and right in a horizontal plane) is pulled to the right so it does not touch the package being tested.

Add the 850 g weight onto the vertical sliding plate.

Allow the horizontal sliding plate to slide down slowly until its bottom lightly touches desired highest point of the package.

Measure the package width in mm (distance from the top of the base plate to the top of the diaper package).

Record the reading that appears on the digital meter.

Remove the 850 g weight.

Raise the horizontal sliding plate away from the diaper package.

Remove the absorbent article package.

Calculation/Reporting

Calculate and report the "In-Bag Stack Height"=(Package Width/Pad Count Per Stack)×10. Report Sample Identification, i.e. complete description of product being tested (product brand name/size).

Report the determined value for each width measurement to the nearest 1 mm. At least five absorbent article packages having the same pad count are measured in this manner for a given product and the in-bag stack height values are aggregated to calculate an average and standard deviation.

Report the Production Date of the measured package (taken from package coding).

Report the Testing Date and Analytical Method used.

All documents cited herein are, in relevant part, incorporated herein by reference; the citation of any document is not to be construed as an admission that it is prior art with respect to the present disclosure.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A disposable absorbent article comprising a bacteriophage composition comprising one or more bacteriophage strains, wherein the bacteriophage composition is in releasable contact with at least a portion of a delivery surface.

2. The disposable absorbent article of claim 1, wherein the disposable absorbent article is selected from the group consisting of diapers, training pants, adult incontinence products, and feminine hygiene products.

3. The disposable absorbent article of claim 2 comprising a component selected from an absorbent core, a topsheet, and a backsheet, wherein the bacteriophage composition is in releasable contact with at least a portion of the component.

4. The disposable absorbent article of claim 3, wherein the component is a topsheet, and wherein a delivery surface is selected from the group consisting of a wearer-facing surface and garment-facing surface of the component.

5. The disposable absorbent article of claim 1, wherein the one or more bacteriophage strains comprises a lytic bacteriophage.

6. The disposable absorbent article of claim 5, wherein the one or more bacteriophage strains is effective against a strain of bacteria of a taxonomic genus selected from the group consisting of *Streptococcus, Escherichia, Salmonella, List-* eria, *Shigella, Campylobacter, Clostridium, Staphylococcus, Pseudomonas, Mycobacterium*, and any combinations thereof.

7. The disposable absorbent article of claim 1 comprising at least about $1 \times 10^1$ PFUs of the one or more bacteriophage strains.

8. The disposable absorbent article of claim 1 comprising from about $1 \times 10^3$ PFUs to about $1 \times 10^8$ PFUs of the one or more bacteriophage strains.

9. The disposable absorbent article of claim 1 comprising from about $1 \times 10^3$ PFUs to about $1 \times 10^6$ PFUs of the one or more bacteriophage strains per square centimeter of a component of the disposable absorbent article.

10. The disposable absorbent article of claim 1 comprising indicia for communication to a user that the bacteriophage composition is present on the disposable absorbent article.

11. The absorbent article of claim 1, wherein the disposable absorbent article comprises a topsheet comprising a skin care composition, and wherein the bacteriophage composition is disposed on the skin care composition.

12. A method of releasably transferring from the disposable absorbent article at least a portion of the one or more bacteriophage to a surface, wherein the surface is human epithelial tissue.

13. The method of claim 12, wherein at least about $1 \times 10^1$ PFUs of the one or more bacteriophage strains is releasably transferred from the disposable absorbent article to the human epithelial tissue.

14. A method of making absorbent articles comprising:
applying a bacteriophage composition to a web; and
using at least a portion of the web to construct at least a portion of an absorbent article.

15. The method of claim 14, wherein the bacteriophage composition is applied to the web via printing.

16. The method of claim 14, wherein the bacteriophage composition is applied to the web via slot coating.

17. A disposable absorbent article comprising a bacteriophage composition comprising one or more bacteriophage strains, wherein the bacteriophage composition is disposed to be released to a wearer of the absorbent article.

18. The disposable absorbent article of claim 17, wherein the absorbent article comprises at least about $1 \times 10^2$ PFUs of the one or more bacteriophage strains.

19. The disposable absorbent article of claim 17, wherein the absorbent article comprises at least about $1 \times 10^3$ PFUs of the one or more bacteriophage strains.

20. The disposable absorbent article of claim 17, wherein the absorbent article comprises at least about $1 \times 10^4$ PFUs of the one or more bacteriophage strains.

* * * * *